US00PP37358P2

(12) United States Plant Patent
Crowther

(10) Patent No.: US PP37,358 P2
(45) Date of Patent: Apr. 7, 2026

(54) ***GEUM* PLANT NAMED 'DEEPGECITRO'**

(50) Latin Name: ***Geum chiloense* x *rivale***
Varietal Denomination: DEEPGECITRO

(71) Applicant: Deeproot Ventures Ltd., Chichester (GB)

(72) Inventor: Timothy Crowther, Clehonger (GB)

(73) Assignee: DEEPROOT VENTURES LTD., Chichester (GB)

( * ) Notice: Subject to any disclaimer, the term of this patent is extended or adjusted under 35 U.S.C. 154(b) by 0 days.

(21) Appl. No.: 19/258,813

(22) Filed: Jul. 2, 2025

(51) Int. Cl.
*A01H 5/02* (2018.01)
*A01H 6/74* (2018.01)

(52) U.S. Cl.
USPC ..... Plt./263.1
CPC ..... *A01H 6/74* (2018.05); *A01H 5/02* (2013.01)

(58) Field of Classification Search
USPC ..... Plt./263.1
See application file for complete search history.

(56) References Cited

U.S. PATENT DOCUMENTS

PP25,351 P2 * 3/2015 Horvath ..... A01H 5/02
Plt./263.1

* cited by examiner

*Primary Examiner* — Karen M Redden
(74) *Attorney, Agent, or Firm* — Weatherly IP Solutions, LLC; James M. Weatherly; Karen P. Bechtold

(57) ABSTRACT

A new cultivar of *Geum* plant named 'DEEPGECITRO' having yellow colored flowers, with fine scarlet colored petal veins, which flowers over a long period, typically from early spring to late fall. The flowers of 'DEEPGECITRO' face upward and outward and semi-double consisting of a cup of five outer overlapping petals together with three smaller inner free petals. The flowers of 'DEEPGECITRO' are yellow in color, with fine scarlet colored petal veins. 'DEEPGECITRO' is hardy in USDA Zone 4, is sterile and does not produce pollen or fruit or seed.

2 Drawing Sheets

Genus and species: *Geum chiloense* x *rivale*.
Variety denomination: 'DEEPGECITRO'.

BACKGROUND OF THE INVENTION

The present invention relates to a new and distinct cultivar of *Geum* plant, commonly named Avens, which is grown as an herbaceous perennial for planting in the garden and landscape or in containers. The new cultivar is known botanically as *Geum chiloense* x *rivale* from the family Rosaceae, and will be referred to hereinafter by the cultivar name 'DEEPGECITRO'.

'DEEPGECITRO' was discovered by the inventor as naturally occurring basal stem sport bearing yellow flowers which was observed by the inventor in summer 2019 as a part of a single plant of the inventor's variety of *Geum* Plant named 'TOTALLY TANGERINE' (U.S. Plant Pat. No. 22,041) which bears orange-peach colored flowers. The sport parent plant of 'Totally Tangerine' was established in-ground in the inventor's garden in Herefordshire, United Kingdom. No further sports of 'Totally Tangerine' have been observed by the inventor since his discovery of 'DEEPGECITRO'.

The inventor carried out the first asexual reproduction of 'DEEPGECITRO' in summer 2019, upon observing the sport. The inventor conducted the asexual propagation his garden nursery in Tenbury Wells, Worcestershire, United Kingdom. The propagation method used was division of the parent plant in order to isolate a division and removal of the plant part, which bore yellow flowers. The inventor removed and planted the yellow-flowering plant part in peat-based growing medium until the plant part was established on its own roots. In spring 2020, the inventor divided the established division and provided that division to a commercial tissue culture laboratory with instructions to establish and multiply the new variety in vitro. Since that time, under careful observation by the inventor and by the tissue culture laboratory, the unique characteristics of 'DEEPGECITRO' have been fixed, stable, uniform, and reproduce true to type in successive generations of asexual reproduction.

SUMMARY

The following represent the distinguishing characteristics of 'DEEPGECITRO'. These traits in combination distinguish 'DEEPGECITRO' as a new and distinct cultivar apart from all other existing varieties of *Geum* known to the inventor. 'DEEPGECITRO' has not been tested under all possible conditions and phenotypic differences may be observed with variations in environmental, climatic, and cultural conditions, however, without any variance in genotype.

1. Except for its yellow colored flowers, 'DEEPGECITRO' exhibits very similar growing characteristics to its sport parent, 'TOTALLY TANGERINE'.
2. 'DEEPGECITRO' flowers over a long period, typically from early spring to late fall. A cool winter encourages more profuse flowering in the coming season.
3. The flowers of 'DEEPGECITRO' face upward and outward.

4. The flowers of 'DEEPGECITRO' are semi-double consisting of a cup of five outer overlapping petals together with three smaller inner free petals.
5. The flowers of 'DEEPGECITRO' are yellow in color, with fine scarlet colored petal veins.
6. After one year of growth, a plant of 'DEEPGECITRO' achieves a height, including the inflorescence, of 85 cm to 90 cm. The foliage mound is 40 cm in height and 50 cm in diameter.
7. 'DEEPGECITRO' is hardy in USDA Zone 4.
8. 'DEEPGECITRO' is sterile and does not produce pollen or fruit or seed.

BRIEF DESCRIPTION OF THE DRAWINGS

The accompanying color drawings illustrate the overall appearance of 'DEEPGECITRO' showing the color of its foliage and flowers as true as it is reasonably possible to obtain in color reproductions of this type. Color in the drawings may differ from color values cited in the detailed botanical description, which accurately describe the actual color of the new variety 'DEEPGECITRO'.

The drawing labeled

The drawing labeled

Figure 1:
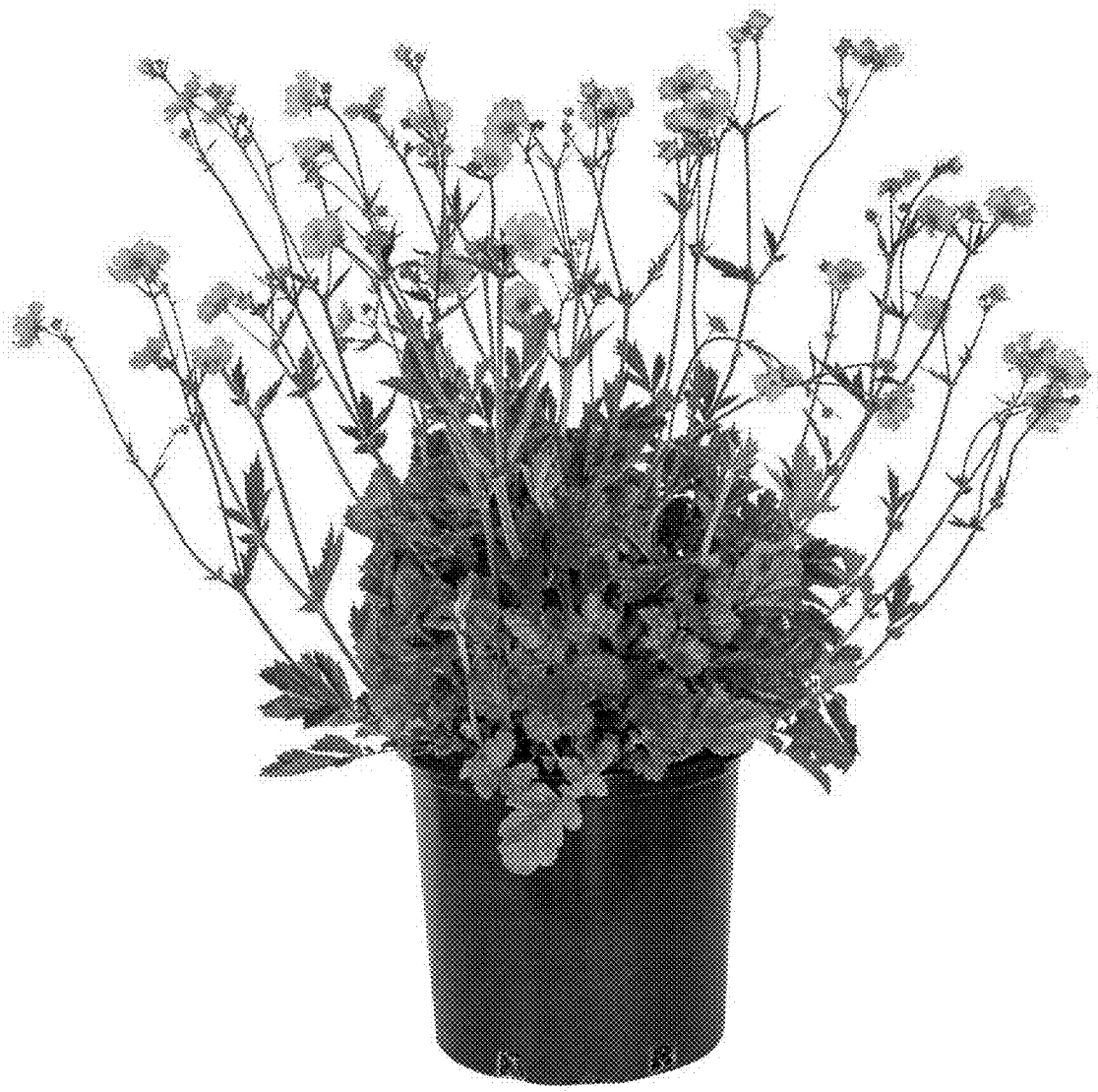
FIG. 1 depicts a two-year-old plant of 'DEEPGECITRO' growing out-of-doors in Tenbury Wells, Worcestershire, United Kingdom.
Figure 2:
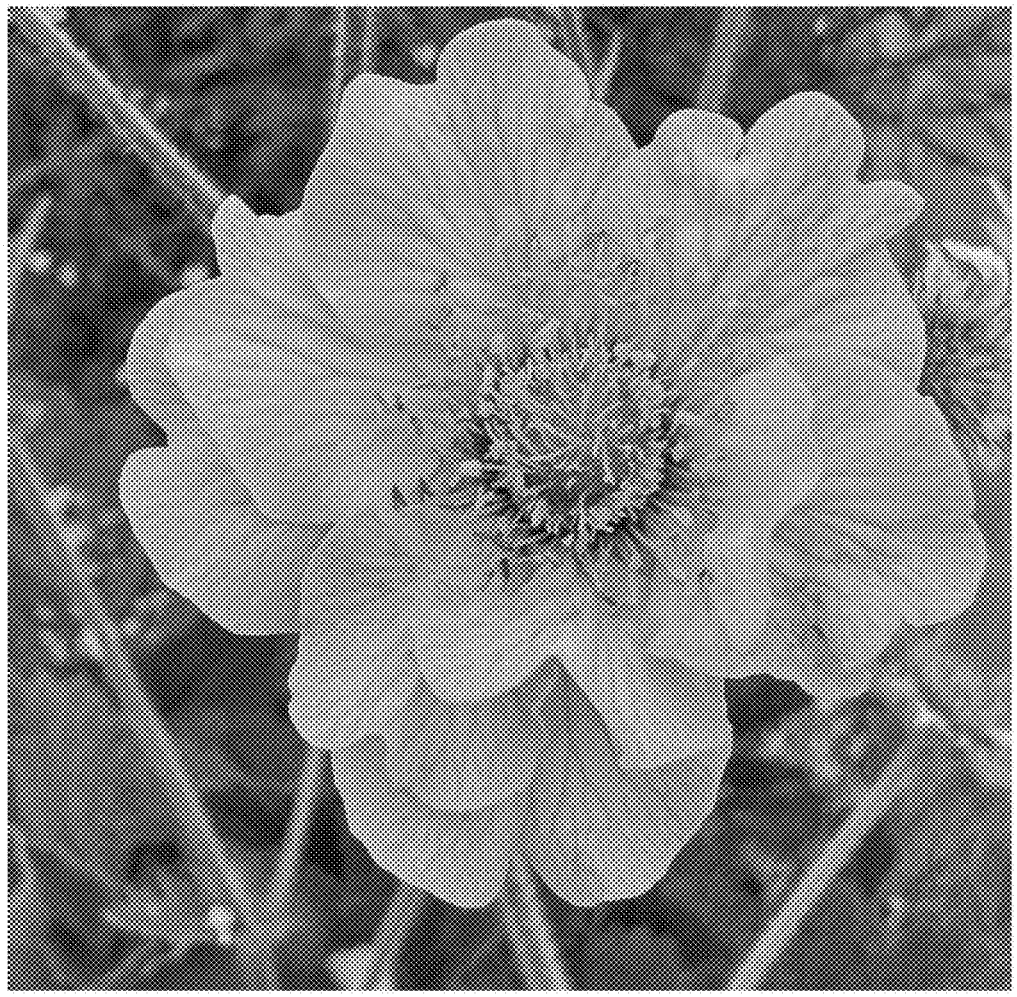
FIG. 2 depicts a close-up view of a flower of a two year-old plant of 'DEEPGECITRO' growing out-of-doors in Tenbury Wells, Worcestershire, United Kingdom.

All drawings have been made using conventional techniques and although colors may appear different from actual colors due to light reflectance, they are as accurate as possible by conventional photography.

DETAILED BOTANICAL DESCRIPTION OF THE PLANT

The following is a detailed description of 'DEEPGECITRO'. Data was collected from a 17 months old plant which had been received in spring 2024 as a young plant propagated in vitro then transplanted into cells of peat-based growing medium by the commercial tissue culture laboratory to be grown and evaluated in a secure private nursery location in Santa Barbara, California. The observed plant had been transplanted into a 3-gallon container and had been grown entirely out-of-doors in Santa Barbara, California without any pruning or pinching or use of any chemical growth regulators.

The color determinations in the description are in accordance with the 2007 edition of The Colour Chart of The Royal Horticultural Society, London, England, except where general color terms of ordinary dictionary significance are used.

The observed plant had been grown naturally in and has remained pest and disease free. Growing requirements are similar to the species.

Botanical classification: *Geum chiloense* x *rivale*.

Family: Rosaceae.

Denomination: 'DEEPGECITRO'.

Common name: Avens.

Parentage: *Geum* 'DEEPGECITRO' was discovered by the inventor as naturally occurring basal stem sport found by the inventor growing on a single in-ground plant of the inventor's variety of *Geum* Plant named 'TOTALLY TANGERINE' (U.S. Plant Pat. No. 22,041).

Plant:

*Commercial category*.—Perennial.

*Recommended container size for garden retail*.—1-litre. Larger containers may be used for display purposes.

*Type*.—Herbaceous perennial.

*Use*.—For garden and landscape and in containers.

*Vigor*.—Vigorous, profuse basal branching and production of foliage.

*Growth habit and shape*.—Clumping and mounding.

*Dimensions of foliage mound*.—40 cm. in height and 50 cm. in width.

*Plant height including inflorescences at peak flowering (late June)*.—85 cm to 90 cm.

*Hardiness*.—USDA Zone 4.

*Propagation*.—Division or tissue culture (in vitro division).

*Time to initiate roots*.—Approximately 30 days are required to produce roots on an initial cutting or tissue culture explant.

*Crop time*.—Approximately 9 months are needed to achieve a finished 1-litre plant in flower from an un-rooted cutting.

*Root system*.—Fibrous. Washed roots colored white NN155D. Roots pubescent, hairs fine, white, NN155D.

*Cultural requirements*.—Well-draining soil or growing medium, plentiful water, and positioned in filtered or full sunlight.

*Seasonal interest*.—Floriferous display of semi-double yellow flowers.

*Disease and pest resistance or susceptibility*.—None known to the inventor.

Stem:

*Branching habit*. Profuse basal stems bearing compound leaves.

*Basal branches*.—Number 120 to 150.

*Stem shape*.—Cylindrical.

*Stem length (average)*.—25 cm to 30 cm.

*Stem diameter*.—8 mm towards base, 5 mm above first (lowest) leaflet.

*Stem color*.—138A.

*Stem surface*.—Pubescent, hairs fine, 1.5 mm to 2.5 mm in length, color silver-white 156D.

Foliage:

*Type*.—Compound evergreen leaves borne along petiolate basal stems from spring into summer.

*Arrangement*.—Cauline.

*Attachment*.—Petiolate.

*Leaf shape*.—Overall deltoid, comprised of one large terminal leaf lobe and two lower (left and right) symmetrical mid-sized lobes.

*Compound leaf dimensions*.—10 cm in length, 9 cm in width.

*Compound leaf apex (is apex of large terminal lobe)*.—Sub-acute.

*Compound leaf base (at conjunction of lower lobes)*.—Cuneate.

*Compound leaf lobes dimensions*.—Terminal lobe: Length 9 cm, width 8.5 cm. Lower lobes (each lobe): 5 cm in length, 6 cm in width.

*Leaf surface color (adaxial)*.—Semi-glossy, 135A.

*Leaf surface color (abaxial)* Matte, 137D.

*Leaf surface texture (adaxial)*.—Semi-glossy, pubescent.

*Leaf surface texture* (*abaxial surface*).—Matte, pubescent. Pubescence prominent on veins.

*Venation*.—Vein pattern: Pinnate. Vein color (adaxial surface): 135A, hairs fine, 1.5 mm in length, color NN155D. Vein color (abaxial surface): Veins raised and pubescent. Vein color 137A, hairs 1.5 mm to 2.5 mm in length, color NN155D. Leaf lobes margin: Evenly dentate, teeth 2 mm in width and 2 mm in height from tooth base to tooth apex. Average of 5 teeth per 1 cm. of margin. Teeth apex: Acuminate with single fine hair, 1.5 mm in length, color 183A. Teeth base: Truncate. Teeth color: 137D except 183A at apex margin.

Leaflets: Petioles terminate with one large compound leaf. Smaller leaves (leaflets) borne singly along petiole.

*Leaflet arrangement*.—Typically, three solitary lower leaflets are borne first, at and above petiole half-length. Two mid-size leaflets are borne in pairs and develop between the uppermost solitary leaflet and the base of the terminal large compound leaf. Solitary leaflets are spaced 7 mm apart.

*Leaflet attachment* (*all*).—Sessile. Mid-sized leaflets are spaced 20 mm apart and 20 mm below large terminal leaf.

*Leaflet shape*.—Deltoid.

*Leaflet dimensions*.—Small solitary leaflets: 12 mm in length, 6 mm in width. Mid-sized leaflets (each): 23 mm in length, 18 mm in width.

*Leaflet color* (*all*).—Adaxial surface 137D, abaxial surface 135A.

*Leaflet surface* (*adaxial*).—Semi-glossy lightly pubescent.

*Leaflet surface* (*abaxial*).—Matte, pubescent.

*Leaflet veins*.—Pinnate, veins raised on abaxial surface with pubescence. Hairs fine, 1.5 mm to 2.5 mm in length.

*Leaflet vein color* (*adaxial surface*).—135A, hairs color NN155D.

*Leaflet vein color* (*abaxial surface*).—137A, color NN155D.

Stipules: Stipules appear as very small solitary sessile leaflets (2 or 3 pairs) attached in the lower (basal) section of each petiole within the foliage canopy.

*Stipule dimensions*.—2 mm in length, 1.5 mm in width.

*Stipule color*.—137A

*Stipule shape*.—Narrowly triangular to lanceolate.

Petioles:

*Description*.—Initially leafless then bearing stipules then small leaflets and terminating with one large compound leaf.

*Petiole shape*.—Sulcate towards stem attachment, terete where leaves are borne.

*Petiole dimensions*.—Length: 30 cm from basal stem attachment to base of uppermost (compound terminal) leaf. Diameter: 5 mm at base, becoming 4 mm where leaves are borne.

*Petiole color*.—154C at base and towards stem, 144B where leaves are borne.

*Petiole texture, strength*.—Fleshy, sulcate, resists bending.

*Petiole surface*.—Pubescent, hairs fine, 2 mm in length, color 156D.

Inflorescence:

*Type*.—Cyme, first bearing solitary peduncle with terminal flowers followed by secondary peduncles each bearing 1 to 3 flowers.

*Inflorescence dimensions*.—

*Height of inflorescence above foliage mound*.—45 cm to 50 cm.

*Inflorescence width*.—8 cm to 20 cm.

*Inflorescence fragrance*.—None observed.

*Inflorescence quantity*.—12 per plant at peak summer flowering.

*Lastingness of inflorescence and flowers*.—Fresh flowers open in each inflorescence over a period of 10-15 days. Each flower lasts for 2-5 days prior to senescence (petal shatter). All flowers in the inflorescence have senesced within 20 days of first opened flower.

Flowers:

*Type*.—Solitary semi-double, consisting of 5 rotate overlapping petals arranged cuplike and 3 inner free petals.

*Aspect*.—Facing upward and outward.

*Bloom season*.—Early spring through fall.

Petals:

*Quantity*.—8 petals (5 basal petals overlapping sideways by 4 mm, forming a cup and enclosing inner free petals.

*Petal shape*.—Orbicular to reniform.

*Petal dimensions*.—12 mm in length (base to apex), 17 mm in width.

*Petal colors* (*excluding veins*).—Yellow-orange 17B (adaxial surface), yellow-orange 17C (abaxial surface).

*Petals fused or unfused* (*all*).—Unfused.

*Petal texture*.—Smooth, semi-glossy, undulating towards margins.

*Self-cleaning or persistent*.—Self-cleaning.

*Petal margins*.—Smooth, entire.

*Petal shape* (*apex*).—Rounded with shallow notch.

*Petal shape* (*base*).—Truncate.

*Petal veins* (*both surfaces*).—Pinnate, fine, color 42B. Colored veins more prominent towards petal center line, becoming fainter towards petal margins.

Buds (observed when sepals first reveal petals):

*Bud shape*.—Obconical.

*Bud dimensions*.—1 cm. in height and 1 cm. in diameter.

*Bud apex*.—Acute.

*Bud base*.—Rounded.

*Bud surface*.—Pubescent.

*Bud color*.—138C (sepal abaxial surface): 44A.

*Bud color* (*revealed petals*).—Ranges between 3A and 6A.

Peduncle:

*Peduncle dimensions* (*range*).—2.50 cm to 7 cm. in length, 2.5 mm to 5 mm. in diameter.

*Peduncle shape*.—Cylindrical.

*Peduncle color*.—166D.

*Peduncle surface*.—Floccose.

Calyx:

*Calyx shape*.—Stellate, sepals recurved.

*Calyx diameter*.—3 cm.

Sepals:

*Sepals*.—5 in number.

*Sepals fused or unfused*.—Fused at base.

*Sepal shape*.—Deltoid.

*Sepal surface*.—Pubescent.

*Sepal margins*.—Entire strongly pubescent, hairs fine, 1 mm in length, color 156D.

*Sepal dimensions*.—9 mm. in length and 6 mm. in width.

*Sepal color* (*abaxial surface*).—138A.

*Sepal color* (*adaxial surface*).—138C.

*Sepal surface* (*adaxial and abaxial*).—Floccose.

*Sepal apex*.—Acute.

*Sepal base*.—Truncate.

Bracteoles:

*Bracteole*.—Tiny, 5 in number, arranged and attached midway between each adjacent sepal.

*Bracteole fused or unfused*.—Unfused.

*Bracteole shape*.—Narrowly elliptic to lanceolate.

*Bracteole margin*.—Entire.

*Bracteole dimensions*.—3 mm. in length and 1 mm. in width.

*Bracteole color*.—137A (adaxial surface), 165B (abaxial surface).

*Bracteole apex*.—Acute.

*Bracteole base*.—Obtuse.

Reproductive organs:

*Stamen*.—Very many: 60 or more in number. Filament dimensions: 6 mm in length, 0.25 mm in diameter. Filament color: 12A. Anthers: Basifixed, ellipsoid, 2 mm in length, 1 mm in width. Anther color: 163B. Pollen color: Has been occasionally observed by the breeder but was not observed on any flowers when the description was taken. Style: Very many: 75 or more in number. Style shape: Filiform, geniculate. Style dimensions: length: 8 mm including geniculate extension, 3 mm to 4 mm. Style color: 172A. Style persistence: Styles remain attached and protruding from the receptacle after flower senescence (petal shatter) as receptacle remains on the plant. Styles protrusion after senescence: 6 mm above receptacle. Style color after senescence: 187B.

*Ovary*.—Ovary position: Inferior. Ovary color: 144C. Ovary shape: Pyramidal. Ovary dimensions: 2.5 mm. in height and 2.5 mm. in width.

Seed: None present. Variety is sterile.

COMPARISON WITH SPORT PARENT

'DEEPGECITRO' is distinguished from the sport parent as described in Table 1.

TABLE 1

| Characteristic | Instant Variety 'DEEPGECITRO' | Sport Parent Variety 'TOTALLY TANGERINE' |
|---|---|---|
| Flower color | Yellow-orange, fine scarlet veins | Peach-orange |

COMPARISON WITH KNOWN COMMERCIAL VARIETY

'DEEPGECITRO' is most similar to the commercial *Geum* plant named 'BANANA DAIQUIRI' (U.S. Plant Pat. No. 25,351) Differences between the two varieties are described in Table 2.

TABLE 2

| Characteristic | Instant Variety 'DEEPGECITRO' | Comparison Variety 'BANANA DAIQUIRI' |
|---|---|---|
| Plant vigor and size | Very vigorous, tall and wide | Compact, smaller foliage mound |
| Flowering | Profuse over long season | Late spring to summer |
| Flower color | Yellow-orange, fine scarlet veins | Lemon-yellow |
| Flower form | Semi-double, 8 petals per flower | Double and single, 10-20 petals per flower |

I claim:

1. A new and distinct variety of *Geum* plant named 'DEEPGECITRO' as described and illustrated herein.

* * * * *